(12) United States Patent
Wang et al.

(10) Patent No.: US 10,493,129 B2
(45) Date of Patent: Dec. 3, 2019

(54) USE OF FIBROBLAST GROWTH FACTOR 2

(71) Applicant: BEIJING INSTITUTE OF MICROBIOLOGY AND EPIDEMIOLOGY, Beijing (CN)

(72) Inventors: Xiliang Wang, Beijing (CN); Chengyu Jiang, Beijing (CN); Penghui Yang, Beijing (CN); Xin Liu, Beijing (CN); Yueqiang Duan, Beijing (CN); Li Xing, Beijing (CN); Chengcai Lai, Beijing (CN)

(73) Assignee: BEIJING INSTITUTE OF MICROBIOLOGY AND EPIDEMIOLOGY, Beijing (CN)

( * ) Notice: Subject to any disclaimer, the term of this patent is extended or adjusted under 35 U.S.C. 154(b) by 0 days.

(21) Appl. No.: 14/910,401

(22) PCT Filed: Aug. 9, 2013

(86) PCT No.: PCT/CN2013/000944
§ 371 (c)(1),
(2) Date: Feb. 5, 2016

(87) PCT Pub. No.: WO2015/017949
PCT Pub. Date: Feb. 12, 2015

(65) Prior Publication Data
US 2017/0216400 A1    Aug. 3, 2017

(51) Int. Cl.
*A61K 38/18* (2006.01)
*G01N 33/68* (2006.01)

(52) U.S. Cl.
CPC ..... *A61K 38/1825* (2013.01); *G01N 33/6893* (2013.01); *G01N 2333/50* (2013.01); *G01N 2800/12* (2013.01)

(58) Field of Classification Search
CPC .......... A61K 38/1825; G01N 2800/12; G01N 2333/50; G01N 33/6893
See application file for complete search history.

(56) References Cited

U.S. PATENT DOCUMENTS

2008/0172751 A1*  7/2008  Kim .................. A01K 67/0275
800/9

FOREIGN PATENT DOCUMENTS

CN          1953765 A         4/2007

OTHER PUBLICATIONS

Lee, et al., "Concise Review: Mesenchymal Stem Cells for Acute Lung Injury: Role of Paracrine Soluble Factors," Stem Cells 29(6): 913-919 (2011).
Murakami et al., "The FGF system has a key role in regulating vascular integrity," J. Clin. Invest. 118(10):3355-3366 (2008).
International Search Report dated Jun. 18, 2014 for PCT/CN2013/000944.

* cited by examiner

*Primary Examiner* — Kaipeen E Yang
(74) *Attorney, Agent, or Firm* — Knobbe, Martens, Olson & Bear, LLP

(57) ABSTRACT

The present invention provides a novel use of fibroblast growth factor 2 (FGF-2), i.e., a use of FGF-2 in preparation of medicine. The uses of the medicine are the following (a) and/or (b) and/or (c): (a) the prevention and/or treatment of lung injury; (b) the prevention and/or treatment of influenza; (c) the prevention and/or treatment of diseases caused by influenza viruses.

6 Claims, 5 Drawing Sheets
Specification includes a Sequence Listing.

USE OF FIBROBLAST GROWTH FACTOR 2

TECHNICAL FIELD

The present invention relates to a novel use of fibroblast growth factor 2.

BACKGROUND ART

The family of fibroblast growth factors (FGFs) includes 23 polymorphic growth factors with associated structures. Fibroblast growth factor-2 (FGF-2), which is one of the members of the FGF family, was extracted from bovine pituitary by American scientist Gospodsrowicz D in 1974, and is widely present in the cells derived from mesoderm and neural ectoderm as well as from various tumor cells. It activates a FGF receptor on the membrane of a target cell, mainly in an autocrine and/or paracrine manner, to induce a series of intracellular signaling, and involves in various physiological and pathological processes such as embryonic development, angiogenesis, nerve regeneration, tumor growth, etc.

FGF-2 has an isoelectric point, PI>9. 0, and is also referred to as a basic fibroblast growth factor (bFGF). The gene of FGF-2 is located in a human chromosome at 4q26, with a full length of 38 kb, comprising 3 exons and 2 introns. The mRNA of FGF-2 has multiple translation initiation sites, which can produce FGF-2 subtypes with various molecular weights, including subtype with a low molecular weight of 18 kd and subtypes with high molecular weights of 22, 22.5, 24 and 34 kd, but the FGF-2 with a low molecular weight of 18 kd which comprises 155 amino acid residues dominates. Low molecular weight subtypes are expressed in cytoplasm and membrane of a cell, while high molecular weight subtypes mainly directly enter into nuclei to function.

Acute lung injury (ALI) is an injury of alveolar epithelial cells and capillary endothelial cells due to a variety of direct and indirect injury factors, which can cause diffuse interstitial and alveolar edema in lung, resulting in acute hypoxic respiratory dysfunction. ALI is pathophysiologically characterized by reduced lung volume, decreased lung compliance, and imbalanced ratio of ventilation/blood flow; clinically characterized by progressive hypoxemia and respiratory distress; and characterized in lung imaging by inhomogeneous exudative lesions, called acute respiratory distress syndrome as it develops into a severe stage (oxygenation index<200). Common ALI-inducing factors are divided into direct and indirect lung injury factors, wherein direct lung injury factors include, for example, severe lung infection induced by viruses, bacteria and fungi, aspiration of gastric contents, lung contusion, oxygen poisoning, etc.; indirect lung injury factors include, for example, sepsis, shock, massive blood transfusion, cardiopulmonary bypass (CPB), disseminated intravascular coagulation (DIC), etc.

Lung injury is clinically characterized by: (1) acute onset, occurring within 12-48 hours after a direct or indirect pulmonary trauma; (2) difficulties to correct hypoxemia after conventional oxygen inhalation; (3) non-specificity of lung signs, hearable moistrales or decreased breath sounds in both lungs at acute phase; (4) early lesions, mainly interstitial, with no significant change in chest x-ray film (C-XF), but occurrence of lung consolidation after progression of disease, characterized by generally increased density, decreased transparency, increased and thickened lung markings, and visiable, discrete, patch-like, density-increased shadows in both lung fields; (5) shadows of diffuse pulmonary infiltrates, with no evidence of cardiac dysfunction.

Lung injury is clinically diagnosed through standards of: (1) acute onset; (2) an oxygenation index $(PaO_2/FiO_2) \leq 200$ mm Hg ((1 mm Hg=0.133 kPa, regardless of positive end expiratory pressure (PEEP) level; (3) patch-like shadows in both lungs shown in anteroposterior C-XF; (4) pulmonary artery wedge pressure $(PAWP) \leq 18$ mm Hg, or no clinical evidence of increased pressure in left atrium. For example, it may be diagnosed as ALI when showing $PaO_2/FiO_2 \leq 300$ mm Hg and meeting other standards described above.

Lung injuries induced by respiratory viruses, bacteria, or fungi are the most common acute respiratory infections in clinic. Among these, influenza is a common and frequent disease affecting extremely widely on people, and there is now a grim situation of cross-species infection by influenza virus. Infection with influenza A virus H1N1 leads to clinical symptoms which are relatively mild in most patients, characterized in typical influenza-like symptoms, and can be recovered naturally. The most common symptoms include cough, fever, sore throat, headache, and other discomforts. Severe pneumonia patients have visible multiple lesion infiltration in C-XF, which can rapidly develop into ARDS, kidney or multi-organ failure. The incidence of influenza A combined with ARDS may be 100 folds of normal influenza. Lung damages are primarily derived from uncontrolled systemic immune response, and like ARDS that is secondary to viral pneumonia, include diffuse alveolar damage, bronchiolar and perivascular lymphocytic infiltration, hyperplastic airway changes, and bronchiolitis obliterans.

Both of clinical and pathological examinations indicate that serious patients may have lesions mainly in the respiratory system. It can be seen from a pathological examination that serious patients may have consolidation in lung, often accompanied with pathological changes such as bleeding, effusion, abscessus, etc. Serous effusion or fibrinous effusion found in alveolar space, accompanied with varied degrees of transparent film formation, which is indicative of diffuse lung injuries. It is currently considered that the basic lesions of pulmonary tissue injuries induced by influenza A virus H1N1 is similar to those of lung in serious cases resulted from other types of influenza, SARS, RSV, adenoviruses, parainfluenza, recently emerged SARS-like viruses, Human avian influenza H7N9, etc, i.e., varied degrees of diffuse pulmonary tissue injuries.

Lipopolysaccharides (LPSs), which are a group of water-soluble and glycosylated lipoplexes, are important ingredients in outer membrane of a gram-negative bacterium, and formed of three parts of lipid A, core polysaccharide and antigen O. LPS have a molecular weight of more than 10000 Daltons, with a complicated structure. Lipid A is a glycolipid contributive to endotoxin activity, covalently linked to a heteropolysaccharide chain. Human is extremely susceptible to bacterial endotoxin, and even a very small amount (1-5 ng/1000 g body weight) of endotoxin can induce an increased body temperature, a fever reaction which often lasts for about 4 hours and then gradually subsides. In the case of a natural infection, because of continuous growth and proliferation of gram-negative bacteria, accompanied with one after another death and release of endotoxin, the fever reaction will last until pathogens are completely eliminated in the body.

Fever reaction is induced by endotoxin because the endotoxin acts on macrophages and the like in bodies to produce cytokines such as interleukin-1, interleukin-6, and tumor necrosis factor-α, etc., which in turns act on the thermotaxic center of hypothalamus in the host, resulting in increased body temperature and fever. Endotoxemia has clinical symptoms mainly depending on host's resistance to endotoxin, and the symptoms and signs thereof can include: fever, a changed number of leukocytes, a bleeding trend, heart failure, renal function insufficiency, liver damage, neurological syndromes, and shock, etc. Endotoxin can cause release of histamine, serotonin, prostaglandin, kinin, and the like, leading to expansion of microcirculation, reduced volume of venous return blood, decreased blood pressure, inadequate tissue perfusion, hypoxia, acidosis, etc.

Fungi can also affect lung tissues and result in lung injuries which may be mainly characterized by fungal inflammation or related diseases in lung and bronchi, and possibly those in pleura or even mediastinum. Pathogenic fungi belong to primary pathogens, which often induce a primary exogenous infection in an individual with normal immune function. Conditioned pathogenic fungi, alternatively called opportunistic fungi, have low pathogenicity, mostly inducing a deep fungal infection in a susceptible host.

Zymosans are macromolecular polysaccharide complexes extracted from yeast cell walls, formed of proteins and carbohydrates. Zymosans can be used to induce inflammations in lab, and the induced reactions thereby mainly include expression of inflammatory cytokines, upregulation of arachidonic acid, phosphorylation of partial proteins and formation of lipositol. Moreover, zymosans are capable of upregulating the expression of cyclin D2, which indicates that zymosans also play a role in the process of activation and proliferation of macrophages.

The infection with LPS in combination with zymosan may be used to simulate ALI induced by septicemia in vivo. Septicemia refers to an acute systemic infection induced by a pathogen or a conditioned pathogen which invades into blood circulation, and then grows and proliferates in blood, thereby producing toxins. Septicemia is one of risk factors of ALI, and one of the characteristics of septicemia-induced lung injury (SLI) is aggregation and activation of polymorphonuclear neutrophils (PMN) in pulmonary microvassels, giving rise to a series of inflammatory reactions and vascular injuries. In this process, bacterial infection, particularly gram-negative bacterial infection may be a key factor for initial inflammatory reaction. Gram-negative bacteria and LPS, after entering into a circulation, produce a LPS-binding protein (LBP), which will bind to a part of phospholipid A of LPS. The LPS-LBP complex bind to CD14 receptors on mononuclear cells, macrophages, and main neutrophils in plasma, to facilitate the translation of coding genes of specific inflammatory factors (such as TNF-a, IL-1, IL-6). The cytokines are secreted into circulation, which is an important biochemical characteristic in a series of inflammatory reactions responsible for septicemia and lung injuries. These cytokines such as IL-1, IL-6, IL-8, IL-10, IL-12, etc. will induce a series of cascade reactions, and participate the process of lung injury. Therefore, use of the infection with LPS in combination with zymosan may allow for a simulation of septicemia-induced lung injury.

To this end, there is already a great and urgent need for developing a new drug for the treatment and/or prevention of lung injuries in the life sciences.

DISCLOSURE OF INVENTION

The present invention provides a new use of FGF-2.

The present invention provides a new use of FGF-2, i.e. a use of FGF-2 in the manufacture of a drug for the use of (a) and/or (b) and/or (c) as follows: (a) preventing and/or treating a lung injury; (b) preventing and/or treating influenza; (c) preventing and/or treating a disease induced by an influenza virus.

The FGF-2 may be a human-derived FGF-2.

The FGF-2 may be the following (A) or (B): a protein as set forth by SEQ ID NO: 1 in the Sequence Listing; (B) a protein derived from (A) with a substitution and/or a deletion and/or an addition of one or more amino acid residues and having the same activity as (A).

The lung injury may be a lung injury induced by a virus and/or a bacterium and/or a fungus. The virus may be an influenza virus, particularly influenza A virus H1N1, more particularly influenza A virus H1N1 BJ501 strain or influenza A virus H1N1 PR8 strain. The bacterium may be a gram-negative bacterium, particularly *Escherichia coli*, more particularly *E. coli* 0111: B4. The fungus may be a yeast, more particularly *Saccharomyces cerevisiae*.

The lung injury may be a lung injury induced by septicemia.

The lung injury may be a lung injury induced by LPS and zymosan A.

The influenza may be influenza A, particularly an influenza induced by influenza A virus H1N1, which may be particularly influenza A virus H1N1 BJ501 strain or influenza A virus H1N1 PR8 strain.

The influenza virus may be influenza A virus H1N1, more particularly influenza A virus H1N1 BJ501 strain or influenza A virus H1N1 PR8 strain.

The present invention also seeks to protect a drug having an active ingredient of FGF-2; for the use of following (a) and/or (b) and/or (c): (a) preventing and/or treating a lung injury; (b) preventing and/or treating influenza; (c) preventing and/or treating a disease induced by an influenza virus.

The FGF-2 may be a human-derived FGF-2.

The FGF-2 may be the following (A) or (B): a protein as set forth by SEQ ID NO: 1 in the Sequence Listing; (B) a protein derived from (A) with a substitution and/or a deletion and/or an addition of one or more amino acid residues and having the same activity as (A).

The lung injury may be a lung injury induced by a virus and/or a bacterium and/or a fungus. The virus may be an influenza virus, particularly influenza A virus H1N1, more particularly influenza A virus H1N1 BJ501 strain or influenza A virus H1N1 PR8 strain. The bacterium may be a gram-negative bacterium, particularly *E. coli*, more particularly *E. coli* 0111: B4. The fungus may be a yeast, more particularly *S. cerevisiae*.

The lung injury may be a lung injury induced by septicemia.

The lung injury may be a lung injury induced by LPS and zymosan A.

The drug may also comprise an additional active ingredient which may be synergistic with the FGF-2. The drug may also comprise a pharmaceutical substance such as a preservative, a stabilizer, a buffer, and the like. The drug may be in a dosage form of an injection, a spray, a nasal drop, an inhalant, or an oral agent.

The influenza may be influenza A, particularly an influenza induced by influenza A virus H1N1, which may be particularly influenza A virus H1N1 BJ501 strain or influenza A virus H1N1 PR8 strain.

The influenza virus may be influenza A virus H1N1, more particularly influenza A virus H1N1 BJ501 strain or influenza A virus H1N1 PR8 strain.

The present invention also seeks to protect a use of FGF-2 in prevention and/or treatment of a lung injury. The FGF-2 may be a human-derived FGF-2.

The FGF-2 may be the following (A) or (B): a protein as set forth by SEQ ID NO: 1 in the Sequence Listing; (B) a protein derived from (A) with a substitution and/or a deletion and/or an addition of one or more amino acid residues and having the same activity as (A).

The lung injury may be a lung injury induced by a virus and/or a bacterium and/or a fungus. The virus may be an influenza virus, particularly influenza A virus H1N1, more particularly influenza A virus H1N1 BJ501 strain or influenza A virus H1N1 PR8 strain. The bacterium may be a gram-negative bacterium, particularly *E. coli*, more particularly *E. coli* 0111: B4. The fungus may be a yeast, more particularly *S. cerevisiae*.

The lung injury may be a lung injury induced by septicemia.

The lung injury may be a lung injury induced by LPS and zymosan A.

The present invention also seeks to protect a use of FGF-2 for preventing and/or treating influenza, or for preventing and/or treating a disease induced by an influenza virus.

The FGF-2 may be a human-derived FGF-2.

The FGF-2 may be one of following (A) or (B): a protein as set forth by SEQ ID NO: 1 in the Sequence Listing; (B) a protein derived from (A) with a substitution and/or a deletion and/or an addition of one or more amino acid residues and having the same activity as (A).

The influenza may be influenza A, particularly an influenza induced by influenza A virus H1N1, which may be particularly influenza A virus H1N1 BJ501 strain or influenza A virus H1N1 PR8 strain.

The influenza virus may be influenza A virus H1N1, more particularly influenza A virus H1N1 BJ501 strain or influenza A virus H1N1 PR8 strain.

The present invention also seeks to protect a use of FGF-2 as a marker of a lung injury, or use of a substance for detecting FGF-2 in aiding diagnosis of a lung injury, or use of a substance for detecting FGF-2 in the manufacture of a product for aiding diagnosis of a lung injury.

The FGF-2 may be a human-derived FGF-2.

The FGF-2 may be the following (A) or (B): a protein as set forth by SEQ ID NO: 1 in the Sequence Listing; (B) a protein derived from (A) with a substitution and/or a deletion and/or an addition of one or more amino acid residues and having the same activity as (A).

The FGF-2 is particularly the FGF-2 in serum, plasma, or a lung lavage fluid.

The lung injury may be a lung injury induced by a virus and/or a bacterium and/or a fungus. The virus may be an influenza virus, particularly influenza A virus H1N1, more particularly influenza A virus H1N1 BJ501 strain or influenza A virus H1N1 PR8 strain. The bacterium may be a gram-negative bacterium, particularly *E. coli*, more particularly *E. coli* 0111: B4. The fungus may be a yeast, more particularly *S. cerevisiae*.

The lung injury may be a lung injury induced by septicemia.

The lung injury may be a lung injury induced by LPS and zymosan A.

In the present invention, a FGF-2 gene knocked-out mouse model and an influenza A virus H1N1 infected mouse model are used to demonstrate the important role of FGF-2 in an acute pathological injury of pulmonary tissues and death of a mouse induced by infection with influenza A virus H1N1, and the important role of an intervention targeting FGF-2 molecules in the treatment of a lung injury, particularly of an injury induced by the infection with influenza A virus H1N1. In the present invention, FGF-2 is used for treating a mouse model infected with influenza A virus H1N1. The results indicate that FGF-2 plays an important role in the protection of a mouse from the acute pathological injury of pulmonary tissues induced by the infection with influenza A virus H1N1. Therefore, it is first demonstrated by the present invention that FGF-2 plays an important role in the pathological process of influenza A, and FGF-2 is capable of preventing or delaying the serious consequences from infection with influenza A virus.

The present invention also uses LPS from a gram-negative bacterium and zymosan A from a yeast to co-infect a mouse, and it is found that an intervention targeting FGF-2 possibly plays an important role in the treatment of the lung injuries induced by infection of LPS from a gram-negative bacterium in combination with zymosan A from *S. cerevisiae*. The present invention uses FGF-2 to treat a mouse model co-infected with LPS and zymosan A, and as a result, it is shown that FGF-2 can exert a significant protection for mice from acute pathological injuries of pulmonary tissues induced by infection with a composition of LPS and zymosan. Therefore, it is for the first time demonstrated by the present invention that a FGF-2 recombinant protein can prevent or delay the serious consequences from co-infection with LPS and zymosan A.

BEST MODES TO CARRY OUT THE INVENTION

Following Examples are intended to facilitate better understanding of the present invention, but not for limiting the present invention. Those experimental methods used in the following Examples are conventional methods, unless otherwise specified. Those experimental materials used in the following Examples are commercially available from a conventional biochemical reagent supplier, unless otherwise specified. Those quantitative tests in the following Examples each were conducted triplicate, with the results averaged. The data is analyzed and processed with software GraphPad Prism 5. In the statistics of survival rate, after being infected with viruses, those mice which died in 24 h are considered as non-specific death, and are excluded from the statistics of survival rate.

C57 BL/6 mice (4-week old): Laboratory Animal Center of The Academy of Military Medical Science. FGF-2 gene knocked-out mice (with a background of SPF grade C57 BL/6 mice): American Jackson Laboratory, Catalog No. 003256. LPS (LPS, from LPS of *E. coli* 0111: B4): Sigma, 
L2630. zymosan A (Zymosan A, from *S. cerevisiae*): Sigma, Z4250. FGF-2 recombinant protein (Human recombinant FGF-2/basic FGF protein): protein sequence is shown as SEQ NO: 1 in the Sequence Listing, encoding gene thereof is shown as SEQ NO: 2 in the Sequence Listing; Millipore, Catalog No. 01-106, when used, it is diluted into desired concentration with PBS buffer.

Influenza A virus H1N1 A strain /Beijing/501/2009 (H1N1) (abbreviated as BJ501 strain): http://www.ncbi.nlm.nih.gov/Taxonomy/Browser/wwwtax.cgi?mode=info&id=6488568&lvl=3&keep=1&srchmode=1&unlock&lin=s; Yang P, Deng J, Li C, Zhang P, Xing L, Li Z, Wang W, Zhao Y, Yan Y, Gu H, Liu X, Zhao Z, Zhang S, Wang X, Jiang C. Characterization of the 2009 pandemic A/Beijing/501/2009 H1N1 influenza strain in human airway epithelial cells and ferrets. PLoS One. 2012; 7(9):e46184. doi: 10.1371/journal.pone.0046184. Epub 2012 Sep. 26.

Influenza A virus H1N1 A strain/Puerto Rico/8/1934 (H1N1) (abbreviated as PR8 strain): http://www.ncbi.nlm.nih.gov/Taxonomy/Browser/wwwtax.cgi?mode=Info&id=211044&lvl=3&lin=f&keep=1&srchmode=1&unlock; Li C, Yang P, Sun Y, Li T, Wang C, Wang Z, Zou Z, Yan Y, Wang W, Wang C, Chen Z, Xing L, Tang C, Ju X, Guo F, Deng J, Zhao Y, Yang P, Tang J, Wang H, Zhao Z, Yin Z, Cao B, Wang X, Jiang C. IL-17 response mediates acute lung injury induced by the 2009 pandemic influenza A (H1N1) virus Cell Res. 2012 March; 22(3):528-38. doi: 10.1038/cr.2011.165. Epub 2011 Oct. 25.

The PBS buffer used in the Examples is 0.01 mol/L PBS buffer, pH7.2, unless otherwise specified.

Example 1. Increased FGF-2 Level in Mouse Lung Lavage Fluid Induced by Influenza A Virus H1N1

For the experimental group (5 of 4-6 weeks old C57 BL/6 mice): each of the mice was securely fixed, and intraperitoneally injected with 50-60 μL of 1 g/100 mL solution of pentobarbital sodium for anesthesia; the anesthetized mice were kept with their head backward and upward leaned to bring their nasal cavities into an upward position, and 10 μL virus solution of BJ501 strain ($10^{5.5}$ $TCID_{50}$/mouse) was added dropwise to their nasal cavity at each side through a pipette; the mice were kept in this posture for 15 seconds, to allow the virus to enter into their respiratory tracts; 24 hours after the infection with BJ501 strain, the mice were killed by means of intraperitoneal injection of excessive anesthetic; the killed mouse was fixed on a small animal operating table, and the skin and bone of its chest were removed, a small opening was cut on its trachea, and 800 μL PBS buffer was injected into the mouse through the opening; finally, lung lavage fluid (LLF) was aspirated by three repeated imbibitions, and detected for the concentration of FGF-2 therein by a Bio-Plex Mouse Cytokine 23-flex kit.

For the control group (5 of 4-6 weeks old C57 BL/6 mice): the mice were treated in the same way as for the experimental group, except that an equal volume of allantoic fluid of chick embryo was used instead of the virus solution of BJ501 strain.

The results are shown in FIG. 1. The mice infected with influenza A virus H1N1 have a FGF-2 concentration in LLF higher than that of the control group (*P<0.05), that is, the expression level of FGF-2 in LLF is significantly higher in the mice infected with influenza A H1N1 than that in the control group. The results indicate that FGF-2 plays an important role in influenza A H1N1 induced lung injury, and an intervention targeting FGF-2 can hold an important position in the treatment of injuries induced by infection with influenza A H1N1.

Example 2. Induction of More Serious ALI by Influenza A Virus H1N1 in FGF-2 Deficient Mice Each of 6 of 4-6 weeks old C57BL/6 mice (or 6 of 4-6 weeks old FGF-2 gene knocked-out mice) was securely fixed, and intraperitoneally injected with 50-60 μL of 1 g/100 mL solution of pentobarbital sodium by a 1 mL sterile syringe for anesthesia; the anesthetized mice were kept with their head backward and upward leaned to bring their nasal cavities into an upward position, a virus solution of BJ501 strain ($10^{5.5}$ $TCID_{50}$/mouse) was added dropwise to their nasal cavity at each side through a pipette; the mice were kept in this posture for 15 seconds, to allow the virus to enter into their respiratory tracts; 5 days after infection with the influenza A virus, the mice were killed by means of intraperitoneal injection of excessive anesthetic; three of the killed mice were fixed on a small animal operating table, and skin and bone of their chest were removed to expose thoracic cavity, from which lung together with heart were removed, and washed with sterile PBS buffer solution to wash off the blood on the surface, and then placed into a paraformaldehyde fixing solution for fixation at room temperature for 48 h, followed by a series of treatments such as embedding, slicing, HE staining; the other three of the killed mice were fixed on a small animal operating table, and skin and bone of their chest were removed to expose thoracic cavity, from which the entire lungs were taken off, subjected to removal of surface blood and excessive connective tissues, and weighed, and the wet weight of the lung was recorded; then, the lungs were placed in a tissue drier at a high temperature of 55° C. and dried; after 24 h, the lungs were taken out and weighed for dry weight when cooled to room temperature, so as to obtain a wet/dry ratio=wet lung weight/dry lung weight.

The results of slice staining are shown in FIG. 2 (×200 folds), wherein A represents the lung tissue of a C57BL/6 mouse, and B represents the lung tissue of a FGF-2 gene knocked-out mouse. In the C57BL/6 mouse infected with influenza A virus H1N1, serious pathological injuries occurred in lung tissue, normal lung tissue structure was destroyed, and the lung markings were disordered, accompanied with pathological injuries such as bleeding, inflammatory effusion, as well as massive red cells, inflammatory cell infiltration, and the like. The FGF-2 gene knocked-out mouse infected with the same titer of virus had more significant pathological injuries in lung tissue, and more significant pathological changes such as bleeding, effusion, inflammatory cell infiltration, or the like, unclear lung marking, and non-intact structure.

The results of "wet/dry ratio" are shown in FIG. 3. The "wet/dry ratio" of lung can reflect the extent of acute pulmonary edema in a mouse. In a FGF-2 gene knocked-out mouse infected with influenza A virus H1N1, the wet/dry ratio of lung was significantly increased than that of a C57BL/6 mouse (*P<0.05), which indicates that knockout of FGF-2 can deteriorate pulmonary edema in a mouse infected with influenza A virus H1N1. The results indicate that more serious ALI can be induced by influenza A virus H1N1 in a FGF-2 deficient mouse.

Example 3. Induction of More Serious ALI by Influenza A Virus H1N1 in FGF-2 Deficient Mice Each of 20 of 4-6 weeks old C57BL/6 mice (or 20 of 4-6 weeks old FGF-2 gene knocked-out mice) was securely fixed, and intraperitoneally injected with 1 mL sterile syringe 50-60 μL of 1 g/100 mL solution of pentobarbital sodium for anesthesia; the anesthetized mice were kept with their head backward and upward leaned to bring their nasal cavities into an upward position, 10 μL virus solution of PR8 strain ($10^{5.5}$ $TCID_{50}$/mouse) was added dropwise to their nasal cavity at each side through a pipette; the mice were kept in this posture for 15 seconds, to allow the virus to enter into their respiratory tracts; 14 of the mice were subjected to survival statistics (the day before the infection with influenza A virus was recorded as Day 0; from the point of the infection with influenza A virus, 24 hours later was recorded Day 1, and so on) and weight monitoring; the remaining 6 mice were killed by means of intraperitoneal injection of excessive anesthetic 5 days after infection with influenza A virus; three of the killed mice were fixed on a small animal operating table, and skin and bone of their chest were removed to expose thoracic cavity, from which lung together with heart were removed, and washed with a sterile PBS buffer solution to wash off the blood on the surface, and then placed into a paraformaldehyde fixing solution for fixation at room temperature for 48 h, followed by a series of treatments such as embedding, slicing, HE staining; the other three of the killed mice were fixed on a small animal operating table, and skin and bone of their chest were removed to expose thoracic cavity, from which their entire lungs were taken off, and subjected to removal of surface blood and excessive connective tissues, weighed, and the wet weight of the lung was recorded; then, the lungs were placed in a tissue drier at a high temperature of 55° C. and dried; after 24 h, the lungs were taken out and weighed for dry weight when cooled to room temperature, so as to obtain a wet/dry ratio=wet lung weight/dry lung weight.

Figure 1:
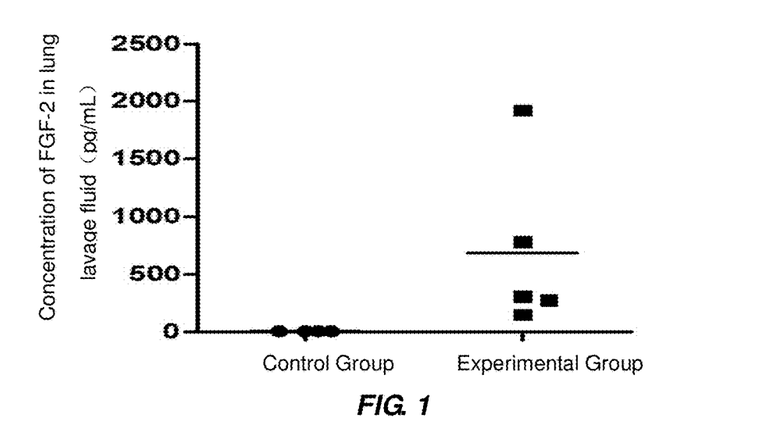
FIG. 1 shows the results in Example 1.
Figure 2:
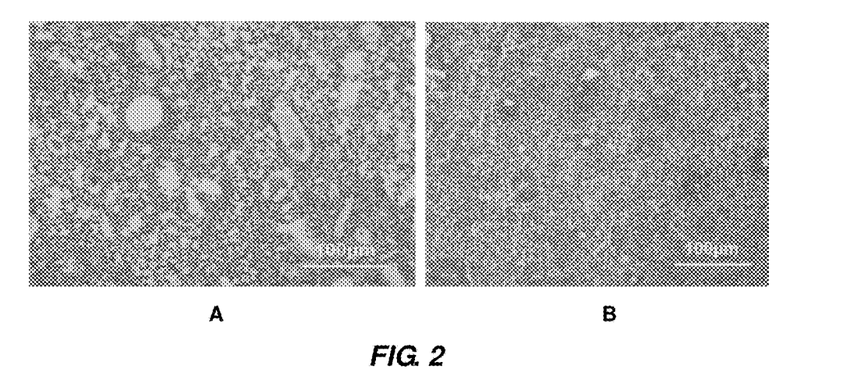
FIG. 2 shows the slice staining results in Example 2.
Figure 3:
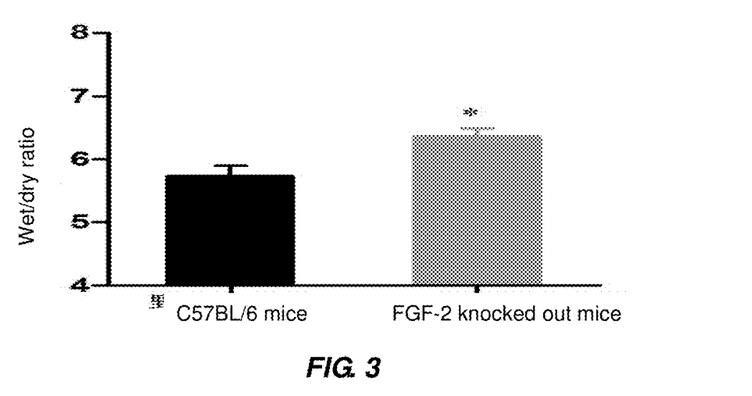
FIG. 3 shows the wet/dry ratio results in Example 2.
Figure 4:
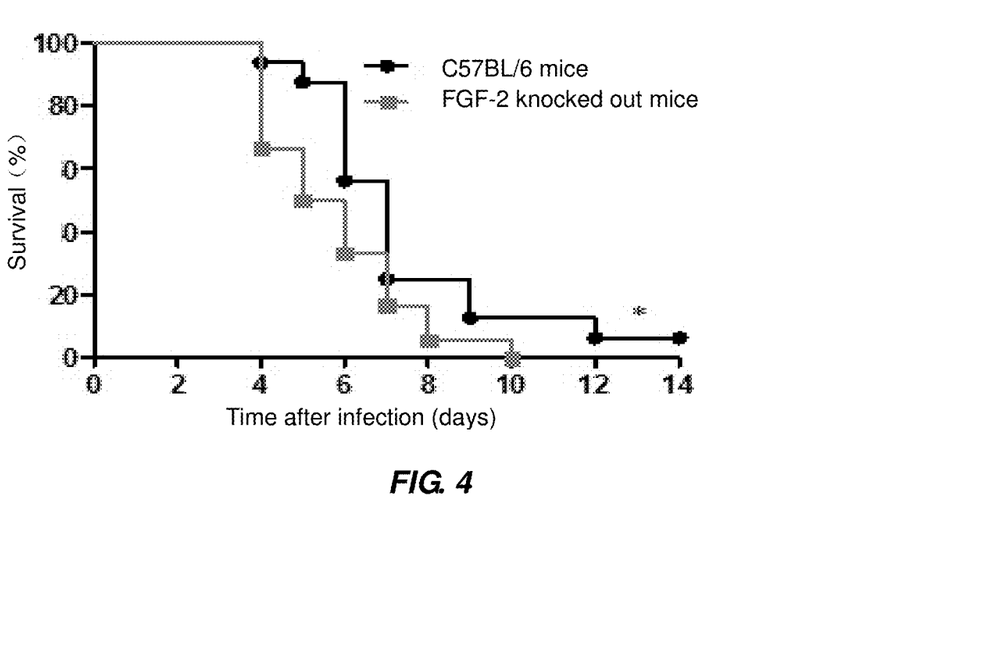
FIG. 4 shows the statistical results of survival rate in Example 3.
Figure 5:
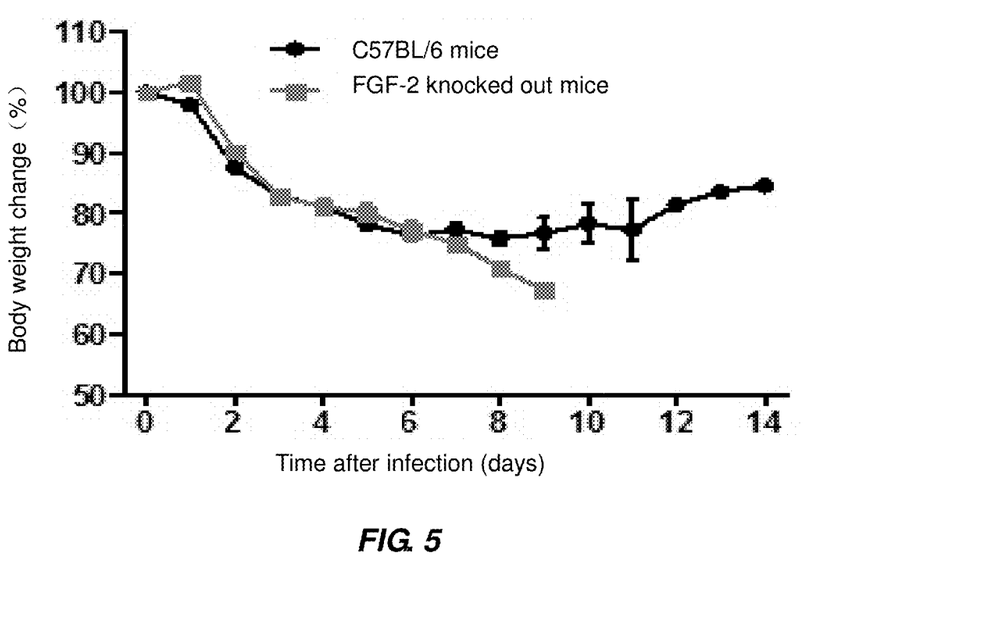
FIG. 5 shows the statistical results of body weight changes in Example 3.

The statistics results of survival rate of mice infected with influenza A virus are shown in FIG. 4. Infected with the same titers of influenza A virus H1N1, the mortality of C57BL/6 mice was significantly lower than the FGF-2 gene knocked-out mice (*P<0.05). The statistical results of body weight change (i.e., a ratio of the body weight at a certain day to that at Day 0) of mice infected with influenza A virus are shown in FIG. 5. Infected with the same titers of influenza A virus H1N1, C57BL/6 mice had a body weight change significantly less than that of the FGF-2 gene knocked-out mice (*P<0.05). The results indicate that FGF-2 plays an essential role in the protection of mice infected with influenza A virus H1N1 from death, and an intervention targeting FGF-2 molecules may play an important role in the protection of treating the one infected with influenza A virus H1N1.

Figure 6:
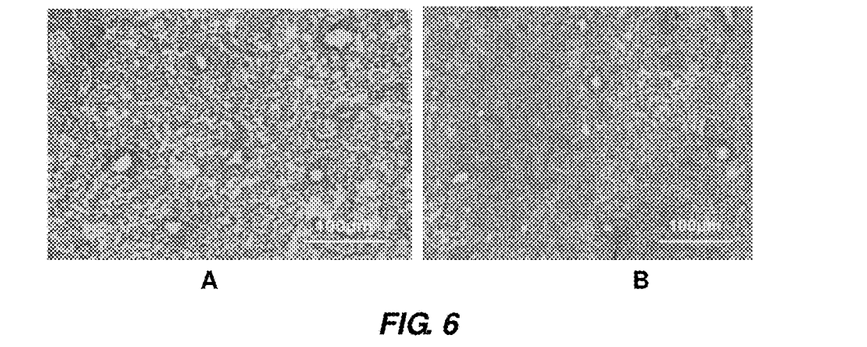
FIG. 6 shows the slice staining results in Example 3.

The results of slice staining are shown in FIG. 6 (×200 folds), wherein A represents the lung tissue of a C57BL/6 mouse, and B represents the lung tissue of a FGF-2 gene knocked-out mouse. In the C57BL/6 mouse infected with influenza A virus H1N1, serious pathological injuries occurred in lung tissue, normal lung tissue structure was destroyed, and lung markings were disordered, accompanied with pathological injuries such as bleeding, inflammatory effusion, as well as massive red cells, inflammatory cell infiltration, and the like. The FGF-2 gene knocked-out mouse infected with the same titer of virus had more significant pathological injuries in lung tissue, and more significant pathological changes such as bleeding, effusion, inflammatory cell infiltration, or the like, unclear lung markings, and non-intact structure.

Figure 7:
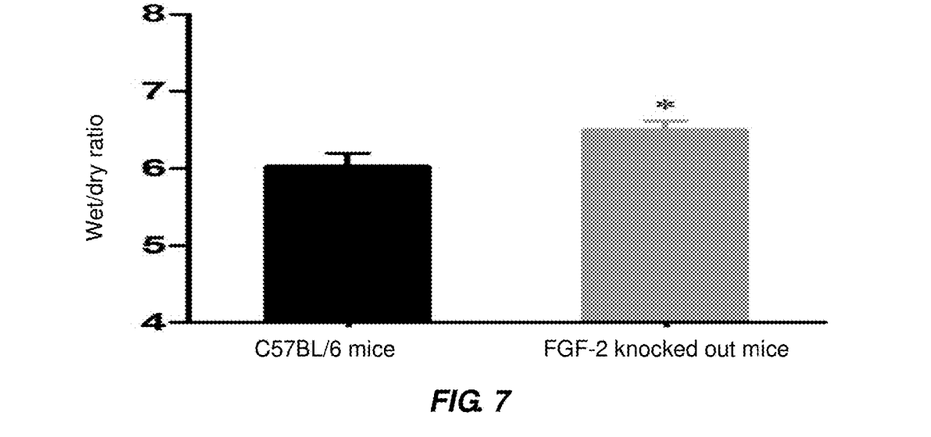
FIG. 7 shows the wet/dry ratio results in Example 3.

The results of "wet/dry ratio" are shown in FIG. 7. In a FGF-2 gene knocked-out mouse infected with influenza A virus H1N1, the wet/dry ratio of lung was significantly increased than that of a C57BL/6 mouse (*P<0.05), which indicates that knockout of FGF-2 can deteriorate pulmonary edema in a mouse infected with influenza A virus H1N1. These results indicate that more serious ALI can be induced by influenza A virus H1N1 in a FGF-2 deficient mouse.

Example 4. Ability of FGF-2 Recombinant Protein to Mitigate Acute Lung Injury Induced by Infection with Influenza A Virus I. Experiment I For a experimental group (10 of 4-6 weeks old C57BL/6 mice): at Day 1, each of the mice was intravenously injected with 100 μl of a solution of FGF-2 recombinant protein (at a protein concentration of 0.5 mg/ml); at Day 2, each of the mice was securely fixed, and intraperitoneally injected with 50-60 μL of 1 g/100 mL solution of pentobarbital sodium by a 1 mL sterile syringe for anesthesia; the anesthetized mice were kept with their head backward and upward leaned to bring their nasal cavities into an upward position, and 10 μL virus solution of PR8 strain ($10^{5.5}$ $TCID_{50}$/mouse) was added dropwise to their nasal cavity at each side through a pipette; the mice were kept in this posture for 15 seconds to allow the virus to enter into their respiratory tract; at Day 3, each of the mice was intravenously injected with 100 μl of the FGF-2 recombinant protein solution (at a protein concentration of 0.5 mg/ml); at Day 5, each of the mice was intravenously injected with 100 μl of the FGF-2 recombinant protein solution (at a protein concentration of 0.5 mg/ml); the survival of the mice was determined daily.

For a control group (10 of 4-6 weeks old C57 BL/6 mice): the mice were treated in the same way except that an equal volume of PBS buffer was used instead of the FGF-2 recombinant protein solution.

Figure 8:
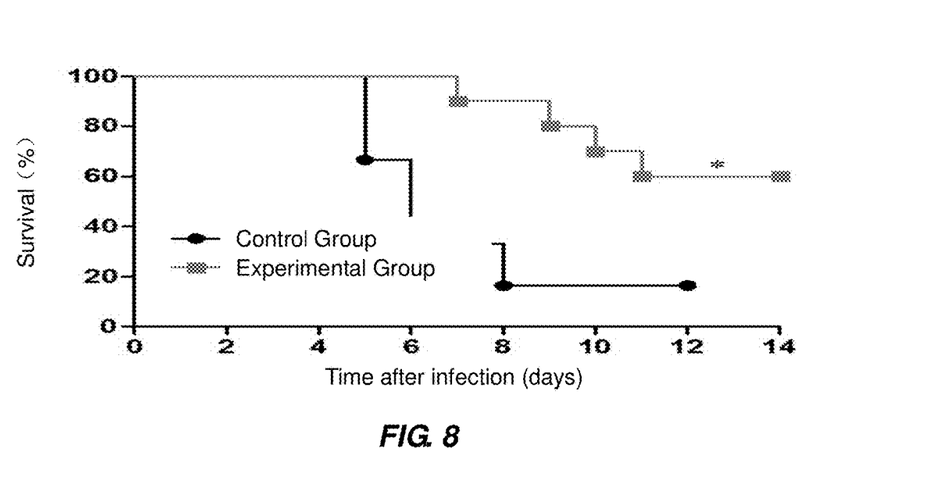
FIG. 8 shows the statistical results of survival rate in Example 4.

The statistic results of the survival rate from Day 1 to Day 14 are shown in FIG. 8. After infected with the same titer of influenza A virus H1N1, the control group had a mortality significantly higher than that of the mice of the experimental group (*P<0.05). The results indicate an important therapeutic effect of FGF-2 in death of the mice infected with influenza A virus H1N1, and an intervention targeting FGF-2 molecules may take an essential part in the recovery of treating the one infected with influenza A virus H1N1.

II. Experiment II

For a experimental group (6 of 4-6 weeks old C57BL/6 mice): at Day 1, each of the mice was intravenously injected with 100 μl of a solution of FGF-2 recombinant protein (at a protein concentration of 0.5 mg/ml); at Day 2, each of the mice was securely fixed, and intraperitoneally injected with 50-60 μL of 1 g/100 mL solution of pentobarbital sodium by a 1 mL sterile syringe for anesthesia; the anesthetized mice were kept with their head backward and upward leaned to bring their nasal cavities into an upward position, and 10 μL virus solution of PR8 strain ($10^{5.5}$ $TCID_{50}$/mouse) was added dropwise to their nasal cavity at each side through a pipette; the mice were kept in this posture for 15 seconds to allow the virus to enter into their respiratory tract; at Day 3, each of the mice was intravenously injected with 100 μl of the FGF-2 recombinant protein solution (at a protein concentration of 0.5 mg/ml), at Day 5, each of the mice was intravenously injected with 100 μl of the FGF-2 recombinant protein solution (at a protein concentration of 0.5 mg/ml), at Day 6, the mice were killed by means of intraperitoneal injection of excessive anesthetic; three of the killed mice were fixed on a small animal operating table, and skin and bone of their chest were removed to expose thoracic cavity, from which lung together with heart were removed, and washed with a sterile PBS buffer solution to wash off the blood on the surface, and then placed into a paraformaldehyde fixing solution for fixation at room temperature for 48 h, followed by a series of treatments such as embedding, slicing, HE staining; the other three of the killed mice were fixed on a small animal operating table, and skin and bone of their chest were removed to expose thoracic cavity, from which their entire lungs were taken off, and subjected to removal of surface blood and excessive connective tissues, weighed and the wet weight of the lung was recorded; then, the lungs were placed in a tissue drier at a high temperature of 55° C. and dried; after 24 h, the lungs were taken out and weighed for dry weight when cooled to the room temperature, so as to obtain a wet/dry ratio=wet lung weight/dry lung weight.

For the control group (6 of 4-6 weeks old C57 BL/6 mice): the mice were similarly treated except that an equal volume of PBS buffer was used instead of the FGF-2 recombinant protein solution.

Figure 9:
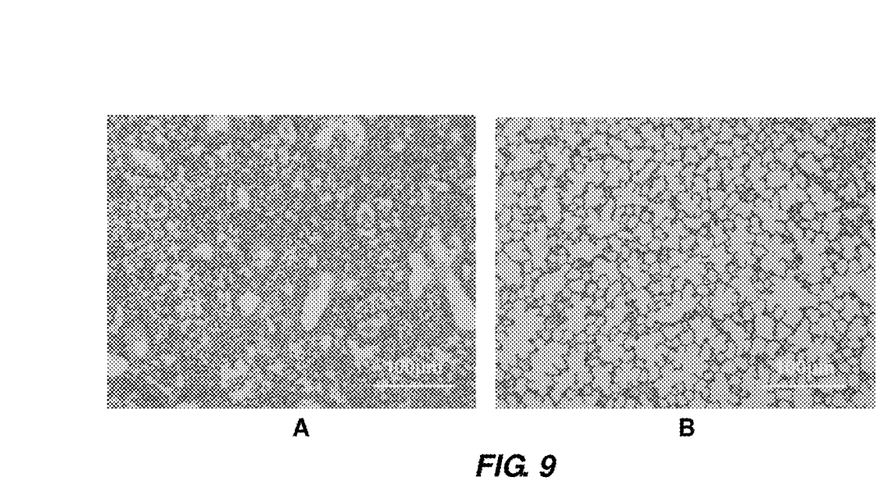
FIG. 9 shows the slice staining results in Example 4.

The results of slice staining are shown in FIG. 9 (×200 folds), wherein A represents the lung tissue of a mouse of the control group, and B represents the lung tissue of a mouse of the experimental group. In the mouse of the control group infected with influenza A virus H1N1, serious pathological injuries occurred in lung tissue, normal lung tissue structure was destroyed, and lung markings were disordered, accompanied with pathological injuries such as bleeding, inflammatory effusion, as well as massive red cells, inflammatory cell infiltration, and the like. However, in the mouse of the experimental group infected with the same titer of virus, neither significant pathological injury of lung tissue, nor significant pathological changes such as bleeding, effusion, inflammatory cell infiltration, or the like, was observed, and their lungs were observed having clear markings and perfect structure. The results indicate that FGF-2 plays an important role in the protection of a mouse from acute pathological injury of lung tissue induced by infection with influenza A virus H1N1.

Figure 10:
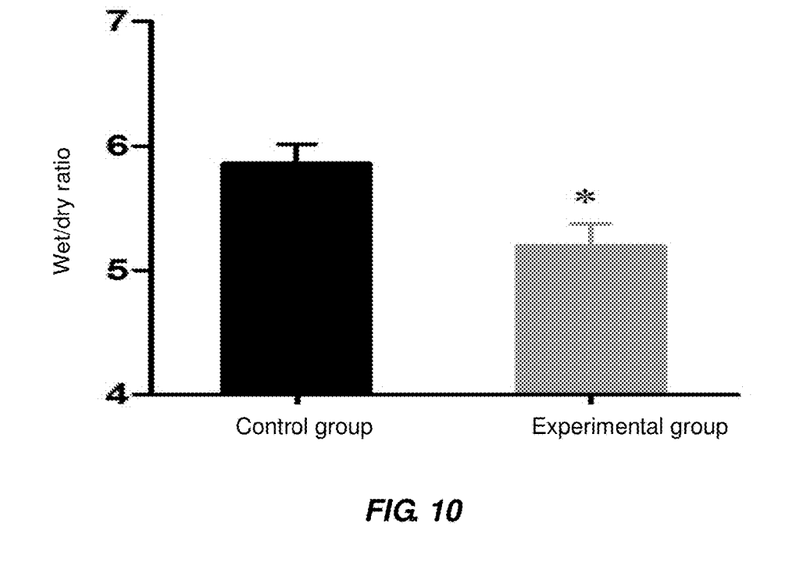
FIG. 10 shows the wet/dry ratio results in Example 4.

The results of wet/dry ratio are shown in FIG. 10. The mice of the experimental group, after being infected with influenza A virus H1N1, had a wet/dry ratio of lung significant lower than that of mice of the control group (*$P<0.05$), which indicates that FGF-2 can substantially mitigate pulmonary edema in a mouse induced by infection with influenza A virus H1N1. The results suggest that FGF-2 plays an important role in the protection from acute pathological injury of lung tissue induced by infection with influenza virus A.

Example 5. Ability of FGF-2 Recombinant Protein to Mitigate Pathological Injury of Mouse Lung Tissue after Co-Infection with LPS and Zymosan A For Group 1 (4 of 4-6 weeks old C57BL/6 mice): each of the mice were intravenously injected with 100 µl of a FGF-2 recombinant protein solution (at a protein content of 50 µg) 12 hours prior to LPS infection, 1 hours prior to LPS infection, and 8 hours after LPS infection, respectively.

Infection: each of the mice was intraperitoneally injected with 50-60 µL of a 1 g/100 mL solution of pentobarbital sodium by a 1 mL sterile syringe for anesthesia; the anesthetized mice were kept with their head backward and upward leaned to bring their nasal cavities into an upward position, and intranasally and dropwise administered with 50 µL of a LPS solution (100 µg LPS in a solvent of PBS buffer); the mice were kept in this posture for 5 minutes to allow the LPS to enter into their respiratory tracts; 1 hour after the infection with LPS, each of the mice was intraperitoneally injected with 50-60 µL of the 1 g/100 mL pentobarbital sodium solution by a 1 mL sterile syringe for anesthesia; the anesthetized mice were kept with their head backward and upward leaned to bring their nasal cavities into an upward position, and intranasally and dropwise administered with 50 µL of a zymosan A solution (60 µg LPS in a solvent of PBS buffer); the mice were kept in this posture for 5 minutes, to allow the LPS to enter into their respiratory tracts.

At 24 hours after the LPS infection, the mice were killed by means of intraperitoneal injection of excessive anesthetic, and fixed on a small animal operating table, and skin and bone of their chest were removed to expose thoracic cavity, from which lung together with heart were removed, and washed with a sterile PBS buffer solution to wash off the blood on the surface, and then placed into a paraformaldehyde fixing solution for fixation at room temperature for 48 h, followed by a series of treatments such as embedding, slicing, HE staining, etc.

Group 2: the mice were treated in the same way as Group 1 except for no injection of FGF-2 recombinant protein solution 12 hours prior to LPS infection, 1 hours prior to LPS infection, and 8 hours after LPS infection.

Group 3: the mice were treated in the same way as Group 1 except that an equal volume of PBS buffer solution was used instead of the LPS solution, and an equal volume of PBS buffer solution was used instead of the zymosan A solution.

Figure 11:
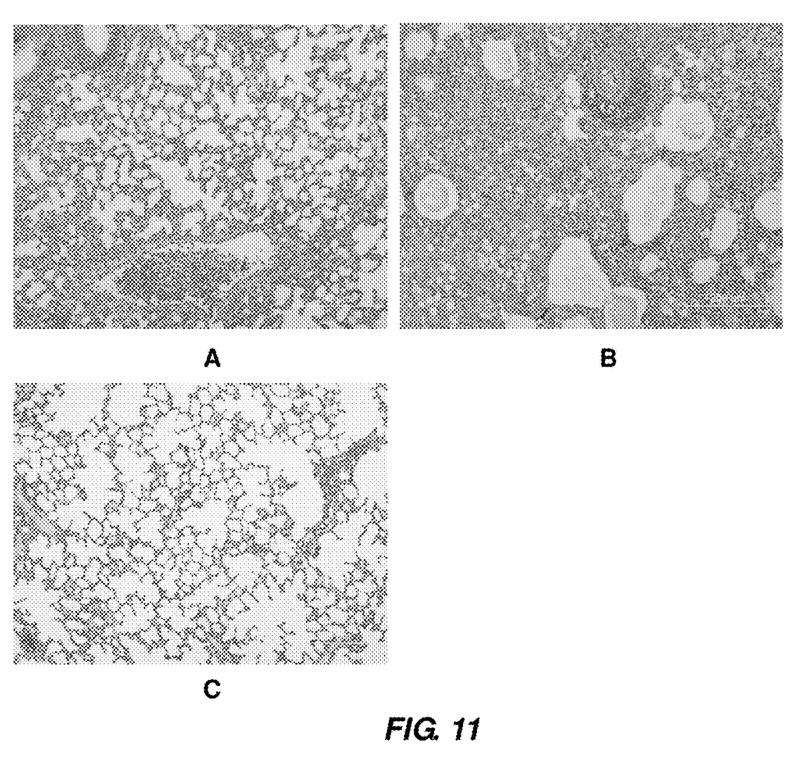
FIG. 11 shows the slice staining results in Example 5.

The results are shown in FIG. 11, wherein A represents Group 1, B represents Group 2, and C represents Group 3. No significant pathological injury and pathological changes such as bleeding, effusion, inflammatory cell infiltration, or the like, but clear lung markings and perfect structure were observed in the lung tissue of the mice of Group 3. Significant pathological injury and pathological changes such as bleeding, effusion, inflammatory cell infiltration, or the like, unclear lung markings, and non-intact structure were observed in the lung tissue of the mice of Group 2. No significant pathological injury and pathological changes such as bleeding, effusion, inflammatory cell infiltration, or the like, but clear lung markings and perfect structure were observed in the lung tissue of the mice of Group 1. The results indicate that FGF-2 plays an important protective role in acute pathological injuries of lung tissue in mouse induced by co-infection with LPS and zymosan A.

INDUSTRIAL APPLICATION

The present invention discloses uses of FGF-2 in the manufacture of a drug for treating and/or preventing lung injury, for preventing and/or treating influenza, and for preventing and/or treating a disease induced by an influenza virus. The present invention may be valuable for the treatment and prevention of above diseases.

What is claimed:

1. A method of protecting a mammal with an influenza infection from an acute lung injury caused by the influenza infection, or a disease induced by the influenza infection or treating an acute lung injury caused by the influenza infection or a disease induced by the influenza infection, said mammal being in need of said protecting or treating, said method comprising administering fibroblast growth factor-2 (FGF-2) to said mammal.

2. The method according to claim 1, wherein the FGF-2 is a human-derived FGF-2.

3. The method according to claim 2, wherein the FGF-2 is a protein having the amino acid sequence set forth in SEQ ID NO: 1.

4. The method according to claim 1, wherein the mammal is in need of the protecting or treating for an acute lung injury.

5. The method according to claim 1, wherein the mammal is in need of the treating for influenza, or the protecting or the treating for a disease induced by an influenza virus.

6. The method according to claim 5, wherein the influenza virus is influenza A virus H1N1.

\* \* \* \* \*

SEQUENCE LISTING

<160> NUMBER OF SEQ ID NOS: 2

<210> SEQ ID NO 1
<211> LENGTH: 155
<212> TYPE: PRT
<213> ORGANISM: Homo sapiens

<400> SEQUENCE: 1

```
Met Ala Ala Gly Ser Ile Thr Thr Leu Pro Ala Leu Pro Glu Asp Gly
1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 2
<211> LENGTH: 468
<212> TYPE: DNA
<213> ORGANISM: Homo sapiens

<400> SEQUENCE: 2

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cgttacctgg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga agctatact ttttcttcca atgtctgcta agagctga                 468
```